United States Patent [19]

Horber et al.

[11] Patent Number: 5,108,450
[45] Date of Patent: Apr. 28, 1992

[54] FEMUR HEAD PROSTHESIS

[75] Inventors: Willi Horber, Zurich; Rudolf Koch, Berlingen, both of Switzerland

[73] Assignee: Sulzer Brothers Limited, Winterthur, Switzerland

[21] Appl. No.: 756,288

[22] Filed: Sep. 6, 1991

[30] Foreign Application Priority Data

Oct. 10, 1990 [CH] Switzerland .......................... 3263/90

[51] Int. Cl.⁵ ............................................... A61F 2/36
[52] U.S. Cl. .......................................... 623/23; 623/18
[58] Field of Search .................... 623/23, 22, 18, 16

[56] References Cited

U.S. PATENT DOCUMENTS

| | | | |
|---|---|---|---|
| 4,266,302 | 5/1981 | Tornier | 623/23 |
| 4,690,489 | 3/1987 | Thompson | 623/16 |
| 4,919,665 | 4/1990 | Homsy | 623/23 X |
| 4,938,770 | 7/1990 | Frey et al. | 623/23 |

FOREIGN PATENT DOCUMENTS

| | | | |
|---|---|---|---|
| 0145938 | 6/1985 | European Pat. Off. | 623/22 |
| 3122730 | 6/1981 | Fed. Rep. of Germany | 623/18 |
| 3904528 | 2/1989 | Fed. Rep. of Germany | 623/18 |
| 2425237 | 12/1979 | France | 623/23 |

*Primary Examiner*—Ronald Frinks
*Attorney, Agent, or Firm*—Kenyon & Kenyon

[57] ABSTRACT

A femur head prosthesis consists of a shaft having several plate springs fixed unilaterally, which are enclosed by a thin-walled and deformable shell body. The shell body is connected to the shaft edge and seals the enclosed volume so as to be impermeable to air. The plate springs are laminated springs, which are separated by slits. The depth of the slits towards the proximal end leaves a narrow unslit yoke part. When an intermittent load occurs, a slight bending of the yoke part results and, within the yoke part, a slight displacement of the plate springs with respect to one another to result in a damping and a non-linear increase in the compressive force.

12 Claims, 2 Drawing Sheets

FEMUR HEAD PROSTHESIS

This invention relates to a femur head prothesis.

Heretofore, various types of femur head prostheses have been known for implanting in femur bones. For example, U.S. Pat. No. 4,650,489 describes a prosthesis formed of a non-perforated sheath, a metallic ball and shaft which makes up a core of the prosthesis and an elastomeric layer between the sheath and the core. This elastomer layer is intended to provide damping to impacts transmitted through the core and is to allow some vertical displacement relative to the sheath. Further, German OS 3904528 describes a prosthesis wherein a sheath is to provide for damping characteristics.

Still other prostheses have been known wherein a shank is provided with slots at a distal end, such as described in European Patent Application 0145938, or with laminated constructions, such as described in German OS 3122730 and French Patent 2,425,237 to facilitate implantation in a bone.

When securing a femur head prosthesis in a cavity of a medullary space of a femur bore which is finished to taper conically inward, without the use of cement, a very precise fashioning of the cavity is required for a primary attachment. The prosthesis should also have a similar elasticity to that of the supporting osseous tissue for the bending forces occurring in the transverse plane, so as to reduce intermittent stresses without local stress peaks to the osseous tissue.

French Patent Specification 2,591,885 shows a shaft made from memory metal which is split in the transverse plane and which, at temperatures below human body temperature, has at least one slit, which tries to expand in the anterior and posterior direction after the insertion of the shaft at body temperature and which is intended to brace the shaft towards the osseous tissue.

French Patent Specification 2,549,717 shows a similar shaft having several tongues, which are prestressed during insertion so as to better secure the shaft.

In both of the above designs, osseous tissue is able to grow into the open slits and thus prevent a return deformation. As a result, it is possible to pull the shaft in the event of a further operation. The rigidity for the braced shaft parts also has to be selected so as to be great enough for tolerable displacements of the shaft surface to occur in the direction of the shaft axis under an intermittent dead load and under the conical centering effect of the medullary space for the osseous tissue.

Accordingly, it is an object of the invention to be able to prestress osseous tissue in an unloaded state under a defined initial stress in large surface regions of a femur head prosthesis.

It is another object of the invention to provide a femur head prosthesis which can effect friction damping with greater intermittent loads occurring.

It is another object of the invention to be able to compensate for an inward deformation of a shaft surface of a femur head prosthesis in the lower region of the shaft.

It is another object of the invention to be able to damp compressive forces imposed upon an implanted femur head prosthesis.

Briefly, the invention provides a femur head prosthesis which is comprised of a shaft having an edge and a plurality of plate springs extending distally from the edge and in spaced relation to each other. In addition, the shaft has a neck extending proximally from the shaft edge and a ball extending from the neck. Still further, the prosthesis includes a thin-walled deformable shell body connected to the edge of the shaft and surrounding the plate springs in sealed relation.

The shaft is constructed so that the plate springs are unilaterally fixed while the shell body encloses the volume occupied by the plate springs so that the volume is impermeable to air.

The springs are constructed for example as laminated springs which are spaced apart from medial to lateral to define parallel slits which extend from posterior to anterior. The springs are deformable inwardly of the shaft so as to contact an adjacent spring particularly during implantation of the prosthesis into a prepared medullary cavity of a femur bone. To this end, the slits are made of variable depth longitudinally of the shaft in order to form springs of variable length.

The springs on the medial side of the shaft are also provided with chamfered terminal surfaces to slidingly engage and enlarge the shell during a displacement of the shaft in a distal direction in a bone cavity.

The deformable shell body may also be creped at least in a region of the springs in order to follow movements of the springs during implantation.

The advantages of the prosthesis are regarded as being that a conical shaft part is provided which is subject to a defined mean minimum initial stress, as long as no load occurs; that if a load is produced by an inner deformation of the shaft, there is a substantially greater rigidity under compression; and that with the inner deformation, frictional work is achieved which reduces the impact energy.

These and other objects and advantages of the invention will become more apparent from the following detailed description taken in conjunction with the accompany drawings wherein.

Figure 1:
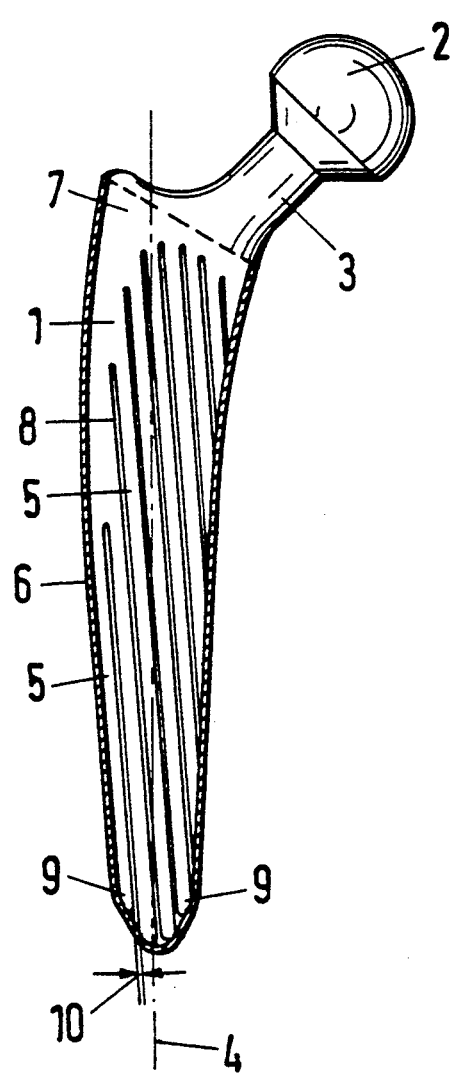
FIG. 1 illustrates a part cross-sectional view of a prosthesis in accordance with the invention taken in a posterior/interior direction.

Referring to FIG. 1, the femur head prosthesis includes a shaft 1 having a ball 2 at an upper end, as viewed, and a neck 3 connecting the shaft 1 with the ball 2. In addition, the shaft 1 extends along a longitudinal axis 4 while the neck 3 extends on an axis forming an angle with the shaft axis 4. The shaft 1 also has a plurality of plate springs 5 which extend distally from an edge (or base) 7 of the shaft adjacent to and integral with the neck 3. These springs 5 are in the form of laminated springs and are spaced apart to define parallel slits 8 therebetween.

Figure 2:
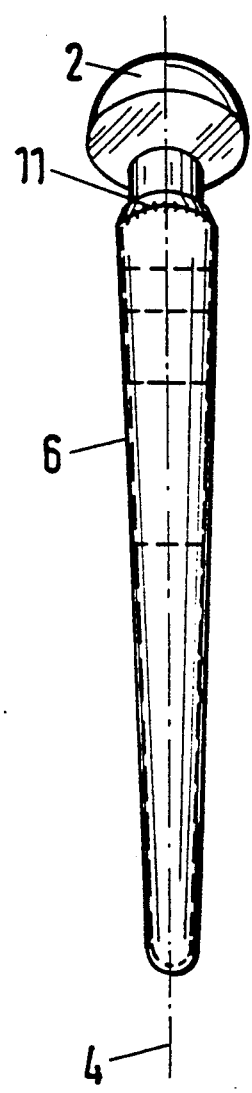
FIG. 2 illustrates a lateral view of the prosthesis of FIG. 1 in a traverse direction.

As indicated in FIG. 1, the plate springs 5 are fixed unilaterally and are enclosed by a thin-walled and deformable shell body 6 which is connected to the edge 7 of the shaft 1 as by a weld 11 (see FIG. 2). This shell body 6 serves to seal in the enclosed volume containing the plate springs 5 so that the enclosed volume is impermeable to air.

The slits 8 in the shaft are of a uniform width 10 and a variable depth longitudinally of the shaft in order to form springs 5 of variable length. In addition, the depth of the slits 8 on the proximal side of the shaft 1 leave a narrow unslit yoke part 14 (see FIG. 3).

As shown in FIG. 1, the springs 5 are disposed at a slight angle to the longitudinal axis 4 of the shaft 1 while being disposed in planes parallel to one another and being spaced apart from medial to lateral. The plates springs 5 are constructed so that the free ends 9 (see FIG. 1) have a small bending strength in the mediolateral direction in comparison with a solid shaft.

Figure 4:
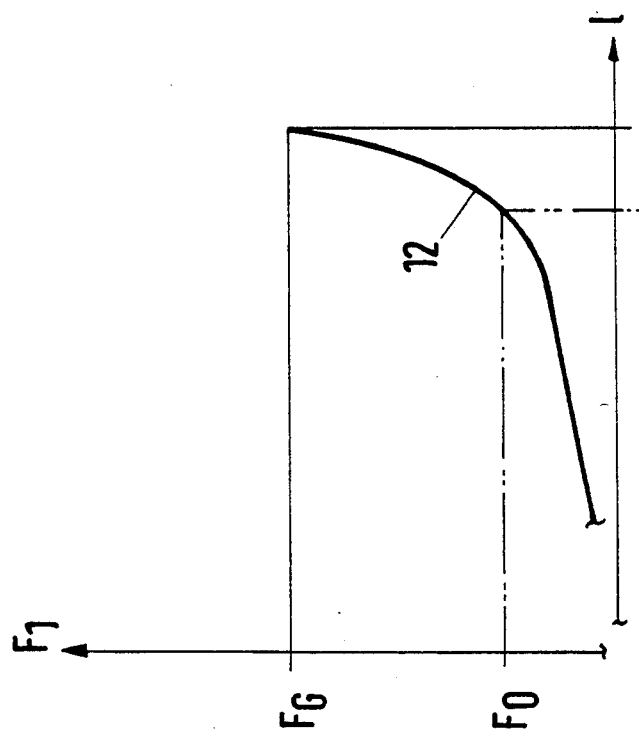
FIG. 4 graphically illustrates a force-deformation diagram of the surface in the lower shaft region for a compressive force in a transverse direction according to FIG. 3.
Figure 3:
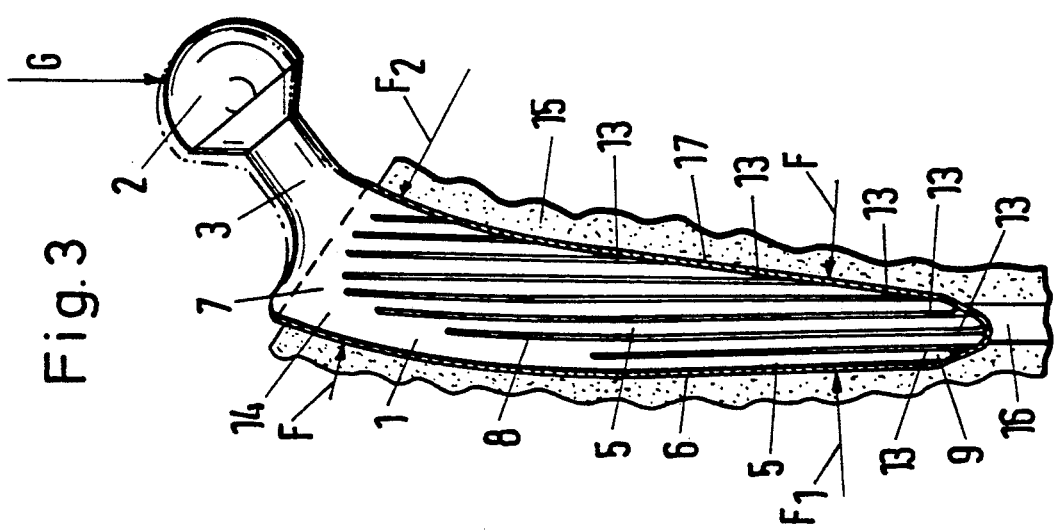
FIG. 3 illustrates a view of the prosthesis of FIG. 1 implanted in a femur in accordance with the invention.

Referring to FIG. 3, wherein like reference characters indicate like parts as above, in the implanted condition without dead load, the laminated springs 5 are deformed when inserted into a prepared medullary space 16 in the inward direction in such a way that they form mutual points of contact with the adjacent laminated springs. When an intermittent dead weight occurs, the result is a slight bending in the yoke part 14 and a slight displacement of the plate springs 5 inside the shell body 6 with respect to one another. This results in a damping and non-linear increase in the compressive force. When inserted into the prepared medullary space 16 of a femur bone, the outer laminated springs are first deformed by one slit width 10, until they touch the inner adjacent plate springs 5 at a point of contact 13, with the latter achieving a continuation of the deformation and also producing resistance. As shown in FIG. 4, a compressive force $F_1$ passes through a first part of a non-linear characteristic 12 for an overproportional increase in the compressive force up to a value $F_0$, until all slit widths 10 in the lower shaft are removed.

The shell body 6, which is preferably creped, is able to follow the deformation of the plate springs 5. The shell 6 is connected to the shaft edge 7 by the welded seam 11 to be impermeable to air, so as to keep abrasive particles away from the osseous tissue 15. The rigidity of the laminated springs 5 and the slit widths 10 are selected so that the ideal prestressing force $F_0$ for the unloaded condition is achieved with the mutual bracing of the plate springs 5.

In FIG. 3 is shown the deformation occurring under a dead load G by a displaced position on the ball end 2. With a rigid shaft, distinct reactions against the direction of the attack of $F_1$ and $F_2$ would occur so as to compensate a bending moment produced by the dead load G. A reaction comprising normal forces F and a reaction comprising frictional forces on the shaft surface, which are equal and are displaced parallel to one another and in the opposite direction to the dead load G, would simultaneously occur. For the slit shaft, the slits 8 extend in the proximal direction into the shaft 1 until there remains a flexible yoke 14 to the neck 3 as the unslit region. Under the dead load G, this yoke 14 performs a deflection which is transmitted to the plate springs 5 as a movement in the direction of the shaft axis 4. The plate springs 5 disposed in the medial direction are thus thrust with their chamfered terminal surfaces 17 deeper in the downward direction in comparison with the adjacent plate springs 5 and compensate for the loss of cross section caused by spring action partly by a conical enlargement with the end surfaces 17. The measurable spring action with a force F is smaller, i.e. the system becomes more inflexible. With an increase in deformation, the force $F_1$ therefore increases overproportionally from $F_0$ to $F_G$. Because of this non-linear increase in the spring tension, the movements between shell body 6 and the fused osseous tissue are slight. It is essential that the front surfaces 17 can slide along the shell body 6—even if this is only to a small extent.

The plate springs 5, which slide and rub against one another in the event of intermittent dead loads and overcome the static friction, absorb impact energy and represent a damping member for the femur bone.

This invention thus provides a femur head prosthesis which is able to prestress the osseous tissue in a femur in an unloaded state under a defined initial stress over large surface regions. Further, with greater intermittent loads, friction damping occurs and, in the lower region of the shaft, there is a compensation of the inward deformation of the shaft surface.

What is claimed is:

1. A femur head prosthesis comprising
   a shaft having an edge and a plurality of plate springs extending distally from said edge and disposed in spaced relation to each other;
   a neck extending proximally from said edge of said shaft;
   a ball extending from said neck; and
   a thin-walled deformable shell body connected to said edge of said shaft and surrounding said springs in sealed relation.

2. A prosthesis as set forth in claim 1 wherein said springs are laminated springs and are spaced apart to define parallel slits.

3. A prosthesis as set forth in claim 2 wherein said springs are deformable inwardly of said shaft to contact an adjacent spring.

4. A prosthesis as set forth in claim 2 wherein said slits are of variable depth longitudinally of said shaft to form springs of variable length.

5. A prosthesis as set forth in claim 1 wherein a plurality of said springs on a medial side of said shaft have chamfered terminal surfaces to slidingly engage and enlarge said shell during a displacement of said shaft in a distal direction in a bone cavity.

6. A prosthesis as set forth in claim 1 wherein said shell is creped at least in a region of said springs to follow movements of said springs during implantation.

7. A prosthesis as set forth in claim 1 wherein said plate springs are disposed at an angle to a longitudinal axis of said shaft.

8. A prosthesis as set forth in claim 1 wherein said plate springs are spaced apart from medial to lateral.

9. A prosthesis As set forth in claim 1 which further comprises a narrow unslit yoke part integral with said edge and on a lateral side of said shaft.

10. A femur head prosthesis comprising
    a shaft having a base, a plurality of plate springs extending distally from said base and disposed in spaced relation to each other to define slits therebetween and a narrow unslit yoke part integral with said base and on a lateral side of said shaft; and
    a thin-walled deformable shell body connected to said base of said shaft and surrounding said springs in sealed relation.

11. A prosthesis as set forth in claim 10 wherein a plurality of said springs on a medial side of said shaft have chamfered terminal surfaces to slidingly engage and enlarge said shell during a displacement of said shaft in a distal direction in a bone cavity.

12. A prosthesis as set forth in claim 11 wherein said shell is creped at least in a region of said springs to follow movements of said springs during implantation.

* * * * *